United States Patent [19]

DeLuca et al.

[11] 4,209,634
[45] Jun. 24, 1980

[54] 1α-HYDROXYCALCIOIC ACID AND ESTERS THEREOF

[75] Inventors: Hector F. DeLuca; Heinrich K. Schnoes; Robert P. Esvelt, all of Madison, Wis.

[73] Assignee: Wisconsin Alumni Research Foundation, Madison, Wis.

[21] Appl. No.: 440

[22] Filed: Dec. 29, 1978

[51] Int. Cl.$^2$ .................. C07C 61/38; C07C 67/74
[52] U.S. Cl. ................................. 560/116; 562/498
[58] Field of Search ...................... 560/116; 562/498

[56] References Cited

PUBLICATIONS

DeLuca et al., Biochem. Chem. Clin. Aspects Relat. Calcium Metal., Proc. Workshop Vit. D3 3rd 1977, pp. 113–122.

Primary Examiner—Robert Gerstl
Attorney, Agent, or Firm—Howard W. Bremer

[57] ABSTRACT

1α-hydroxycalcioic acid. The compound displays antirachitic (vitamin D-like) activity and would find application in disease states characterized by adverse calcium-phosphorous balance or behavior.

3 Claims, No Drawings

1α-HYDROXYCALCIOIC ACID AND ESTERS THEREOF

The invention described herein was made in the course of work under a grant or award from the Department of Health, Education, and Welfare.

The invention relates to a compound which are characterized by vitamin D-like activity.

More specifically, this invention relates to a derivatives of vitamin $D_3$.

Still more specifically, this invention relates to 1α,3β-dihydroxy-9,10-seco-23-norchola-5,7,10(19)-trien-24-oic acid (1α-hydroxycalcioic acid) and methyl 1α,3β,-dihydroxy-9,10,-seco-23-norchola-5,7,10(19)-trien-24-oate.

The antirachitic activity of the D vitamins, and especially vitamin $D_3$, and their application as nutritional supplements is well known.

It is also now well known that to be effective these vitamins must be metabolized in vivo to express the physiological functions with which they are associated. The vitamin is first hydroxylated in the liver to form 25-hydroxy-vitamin D, considered to be the major circulating metabolite in the blood stream. This compound may then be further hydroxylated in the kidney, primarily producing 1α,25-dihydroxyvitamin D or 24,25-dihydroxyvitamin D. The 1α-hydroxylated form of vitamin D is generally considered to be the physiologically active or hormonal form of the vitamin, and to be responsible for what are termed vitamin D-like activities, such as increasing intestinal absorption of calcium and phosphate, mobilizing bone mineral, and retaining calcium in the kidneys. The possibility remains, however, that further metabolism of 1α,25-dihydroxyvitamin D is required to elicit any or all of these responses.

A derivative of vitamin D has now been found which displays some antirachitic activity and which, it is believed, may be the metabolically active form of the vitamin responsible for some of the biological responses mentioned above. This compound has been identified as 1α,3β-dihydroxy-9,10-seco-23-norchola-5,7,10(19)-trien-24-oic acid, more conveniently referred to herein as 1α-hydroxycalcioic acid or 1α(OH)-23(COOH)D. The rapid formation and the high yields in which it is generated in vivo from 1,25-dihydroxycholecalciferol are consistent with the belief that this acidic derivative is perhaps the metabolically active form of the vitamin responsible for some of the biological responses which vitamin-D elicits.

ISOLATION AND IDENTIFICATION

Each of 57 male albino rats in the weight range 200-250 grams was intrajugularly administered 1 µg of 1α,25-dihydroxyvitamin $D_3$ containing $3.65 \times 10^5$ dpm [3α³H] 1α,25-dihydroxyvitamin $D_3$ in 0.1 ml ethanol. The tritiated vitamin was added in order to follow the metabolite through chromatography and to compute recoveries by scintillation counting of aliquots.

Six hours following dosing, the animals were sacrificed by decapitation and their livers were removed and stored on ice. After adding an equal volume of distilled water to the 460 grams of recovered livers, homogenization was effected with a Brinkman Polytron homogenizer (Brinkman Instruments, Inc., Westbury, N.Y.). The homogenate was frozen in round-bottom flasks and lyophyllized requiring yielding 136.4 grams of dry tissue.

The lyophyllized livers were twice extracted for 24 hours at 4° C. with 1:1 chloroform:methanol, followed by filtration. The resultant residue was rinsed with 800 ml methanol, residual solvent being pressed out on the filter. The extracts were combined and evaporated on a rotary evaporator.

The residue from the evaporation was partitioned in a system containing 100 ml $H_2O$:200 ml methanol:200 ml chloroform. The aqueous layer was rendered alkaline (pH 8.5) with ammonium hydroxide before partitioning. The aqueous phase was washed by the addition of 25 ml chloroform and repartitioned. The initial chloroform phase was washed with 90 ml of water (pH 8.5) and 140 ml of methanol. The chloroform phases from the partitionings were combined and found to contain 2.1% of the dosed tritium whereas the combined aqueous phases contained 6.0% of the dosed tritium.

The aqueous phases were evaporated to dryness on a rotary evaporator using ethanol to azeotrope residual water. The residue was filtered in 150 ml of 95% ethanol to remove precipitated proteins.

The filtrate was evaporated to dryness, the recovered material was suspended in 40 ml of 95% methanol and then chromatographed on a $3 \times 17$ cm DEAE Sephadex A-25 (a chromatographic material marketed by Pharmacia Corporation, Piscataway, N.J. and comprising diethyl amino ethyl groups bonded by ether linkage to the glucose residues of cross-linked dextran beads) column. The DEAE column was prepared by pre-equilibration with 0.3 M ammonium bicarbonate in 80% methanol followed by extensive rinsing with 95% methanol. Chromatography was performed by elution, in succession, with 200 ml 95% methanol followed by 400 ml 0.1 M ammonium bicarbonate in 90% methanol and then 200 ml 0.3 M ammonium carbonate. The charged peak of radioactivity, eluted with 0.1 M ammonium bicarbonate and was detected by scintillation counting of fraction aliquots, was recovered by combining elution volumes 374 through 594 ml. This peak was found to contain 72% of the aqueous phase tritium, representing 5.2% of the dosed tritium. The charged peak from DEAE was dissolved in 10 ml methanol and chromatographed on a $2 \times 57$ cm LH-20 Sephadex (a hydroxypropyl ether derivative of polydextran marketed by Pharmacia Corporation, Piscataway, N.J.) column equilibrated and eluted with methanol. The peak fractions eluting between 110 and 170 ml were combined, representing a 65% recovery of radioactivity. This sample was evaporated to dryness and then dissolved in 7 ml methanol.

Diazomethane (generated by standard methods and recovered in an ether solution) was added to the dissolved sample at room temperature to the retention of a yellow color, indicating an excess of the methylating agent. The solvents were evaporated under a stream of nitrogen and the residue was partitioned in 20 ml $H_2O$ (pH 85):40 ml methanol:40 ml chloroform. It was found that methyl esterification had proceeded in 99% yield as computed from chloroform-soluble radioactivity. The chloroform phase was evaporated and chromatographed on a $1 \times 57$ cm LH-20 Sephadex column equilibrated and eluted with 40% hexane in chloroform. 71% of the chloroform soluble radioactivity was recovered in a peak eluting between 94 and 126 ml. These peak fractions were combined and evaporated.

High pressure liquid chromatography (HPLC) was performed on a Waters model ALP/GPC 204 instrument (Waters Associates, Milford, MA.) equipped with a model 440 absorbance detector monitoring at 254 nm. The methylated peak from the LH-20 column was injected into a 4.6 mm×25 cm Zorbax ODS (octadecyl silane bonded to silica beads available through the Du Pont Co., Wilmington, Del.) HPLC column equilibrated in 30% H₂O in methanol and operated at 4300 psi with a 2 ml per min. flow rate. The region eluting between 36 and 48 ml was collected, giving an 89% recovery of radioactivity. This collected sample was chromatographed on a straight phase HPLC system consisting of a 4.6 mm×25 cm Zorbax SIL (available through the Du Pont Co., Wilmington, Del.) column equilibrated in 7% 2-propanol in hexane and operated at 1400 psi with a 2 ml per min. flow rate. A sharp, symmetrical u.v. absorbance peak at 42.5 ml, separated by baseline absorbance on both sides, demonstrated the purity of the metabolite. Elution volumes 40–45.5 ml were combined, with a recovery of radioactivity of 92% for this column. This peak contained 281 nanomoles of the metabolite, representing 25.3% of the aqueous soluble tritium, and 2.04% of the dosed tritium.

The ultraviolet spectrum, obtained on a Beckmann model 24 recording spectrophotometer (Beckman Instrument, Inc., Fullerton, Calif.), demonstrated an absorbance maximum at 265 nm and a spectral shape characteristic of the vitamin D triene.

To ensure purity the sample was again chromatographed on the straight phase HPLC system immediately before mass spectroscopy. A low resolution mass spectrum was obtained using an AEI-MS9 (Associated Electrical Industries) mass spectrometer coupled with a DS-50 data system (Scientific Data Systems). The spectrum, showing prominent peaks at M/e 388 (10.4% of base peak), 370 (13.6%), 357 (1.6%), 352 (9.6%), 314 (1.7%), 287 (1.4%), 269 (1.6%), 251 (3.8%), 152 (18.0%) and 134 (100%), proved that the compound isolated is methyl 1α,3β-dihydroxy-9,10-seco-23-norchola5,7,10(19)-trien-24-oate (methyl 12-hydroxy calcioate).

This compound has the following structure:

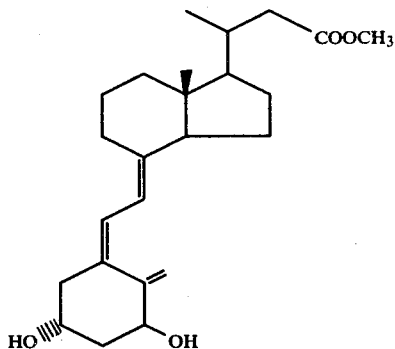

The identity of the compound was established by the following criteria: The ultraviolet spectrum demonstrates an intact vitamin D cis-triene. The molecular ion at M/e 388 is consistent with this structure. The prominent peaks at M/e 370 and 352 represent losses of one or both A-ring hydroxyls. That the A-ring contains both hydroxyl functions and is unaltered from the 1α,25-dihydroxyvitamin D A-ring is confirmed by the fragments at M/e 152 and 134. The ions at M/e 287, 269, and 251 represent the loss of the side chain and subsequent loss of one or both A-ring hydroxyls respectively, demonstrating unaltered C and D rings and an intact 18 methyl. Finally, the fragment at M/e 314 represents a McLafferty rearrangement with loss of $C_3H_6O_2$, demonstrating that the methyl ester moiety is on the 23-carbon and not at the 21-carbon. Unreported peaks in the spectrum are consistent with this structure.

In the methods outlined above, the compound isolated is the methyl ester of the natural product. This ester group can be hydrolysed by the addition of 10% KOH in 90% methanol and warming at 50° C. under nitrogen for 60 minutes. The free acid can be obtained by slowly lowering the pH to pH 6 with 1 N hydrochloric acid, evaporating the solvents and suspending the mixture in 95% ethanol. The resultant suspension is filtered to remove the KCl, yielding 1α,3b-dihydroxy-9,10-seco-23-norchola-5,7,10(19)-trien-24-24-oic acid) in the ethanol solution. This compound is depicted by the following structure:

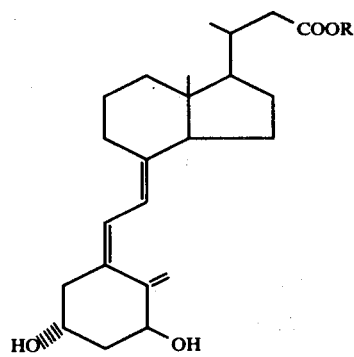

If desired, this compound can be readily obtained in crystalline form by crystallization from alcoholic solvents, e.g. methanol.

In the foregoing description all scintillation counts were obtained with a model 3255 liquid scintillation counter available from Packard Instruments, Downers Grove, Illinois.

Instead of converting the methyl ester to the acid (1α-hydroxycalcioic acid), it can, if desired, be converted to other alkyl esters in which the methyl group is replaced by such groups as ethyl, propyl, butyl, or benzyl. For example, treatment of the methyl ester with sodium ethoxide results in trans-esterification with the formation of the corresponding ethyl ester (ethyl-1α-hydroxycalcioate). Similarly, the propyl, butyl and benzyl esters can be obtained by treating the methyl ester with the appropriate sodium alcoholate.

Alternatively these various esters can be prepared from the acid by treatment with the appropriate alcohol, (e.g. methanol, ethanol, propanol, butanol or benzyl alcohol) in the presence of a suitable condensing reagent, such as a carbodimiide (e.g. dicyclohexylcarbodiimide).

The trans-esterification referred to above and the conversion of the acid to the ester along with reactants appropriate to and which will accomplish the reactions are well known to those skilled in the art.

Thus, the compounds of this invention have the general formula

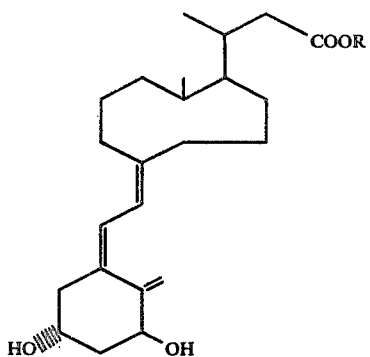

where R is selected from the group consisting of hydrogen, a hydrocarbon chain having from 1 to about 4 carbon atoms and benzyl.

BIOLOGICAL ACTIVITY

Line test assay or rickets cure test

The biological activity of the compound was ascertained as described in U.S. Pharmacopeia, 14th Revision [Mack Publishing Co., Easton Pa. (1955)]. The 1α-hydroxycalcioic acid was administered i.p. daily for six days at a daily dose of 12 ng. in a propylene glycol vehicle. Controls received only the propylene glycol. The results obtained are shown in Table 1 below expressed as units of antirachitic activity per μg of compound.

TABLE I

|  | Rat # | Activity | Average |
|---|---|---|---|
| Control | 1 | 0 | |
|  | 2 | 0 | |
|  | 3 | 0 | |
|  | 4 | 0 | 0.0 |
|  | 5 | 0 | |
|  | 6 | 0 | |

TABLE I-continued

|  | Rat # | Activity | Average |
|---|---|---|---|
| 1α(OH)-23(COOH)D | 1 | 7.0 | |
|  | 2 | 14.0 | |
|  | 3 | 14.0 | |
|  | 4 | 0 | 7 ± 3 |
|  | 5 | 0 | |

It is evident from the foregoing data that 1α-hydroxycalcioic acid displays antirachitic activity.

Moreover, its rapid production in high yield within a few hours after administration of 1,25-dihydroxyvitamin $D_3$ (1,25-dihydroxycholecalciferol), as pointed out hereinbefore, evidences that this compound is a physiologically active metabolite in the vitamin D hormonal system.

What is claimed is:

1. Compounds having the formula

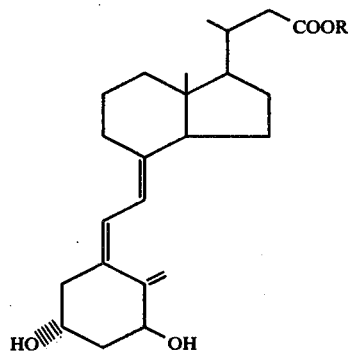

where R is selected from the group consisting of hydrogen, a hydrocarbon chain having from 1 to about 4 carbon atoms and benzyl.

2. A compound according to claim 1 wherein R is hydrogen.

3. A compound according to claim 1 wherein R is methyl.

* * * * *